United States Patent
Webb et al.

(10) Patent No.: US 6,452,022 B1
(45) Date of Patent: Sep. 17, 2002

(54) METHOD FOR PREPARING SUBSTITUTED 4-PHENYL-4-CYANOCYCLOHEXANOIC ACIDS

(75) Inventors: Kevin Webb, Newtown, CT (US); Wilford Mendelson, King of Prussia; Jianhao Chen, Audubon, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/005,547

(22) Filed: Nov. 8, 2001

Related U.S. Application Data

(62) Division of application No. 09/529,235, filed as application No. PCT/US98/21061 on Oct. 7, 1998.
(60) Provisional application No. 60/061,613, filed on Oct. 10, 1997.

(51) Int. Cl.$^7$ .............................................. C07D 303/00
(52) U.S. Cl. .......................... 549/332; 560/59; 558/409; 564/163; 514/417; 514/475; 514/520
(58) Field of Search ................................. 514/417, 475, 514/320; 549/332; 558/409; 560/103, 59; 564/163

(56) References Cited

U.S. PATENT DOCUMENTS 6,337,408 B1 * 1/2002 Allen et al. .................. 549/332

FOREIGN PATENT DOCUMENTS

WO          09/533368          3/2000

* cited by examiner

Primary Examiner—Paul J. Killos
Assistant Examiner—Taylor Victor Oh
(74) Attorney, Agent, or Firm—James M. Kanagy; Charles M. Kinzig

(57) ABSTRACT

This invention relates to a method of preparing a compound type where at least one of R' or R" is a carboxyl group (I) by treating a compound of formula (II) with a Group I(a) or Group II(a) metal halide, with an aprotic dipolar amide-based solvent and water.

8 Claims, No Drawings

METHOD FOR PREPARING SUBSTITUTED 4-PHENYL-4-CYANOCYCLOHEXANOIC ACIDS

CROSS REFERENCES TO RELATED APPLICATION

This application is a divisional of U.S. application Ser. No. 09/529,235 filed Apr. 7, 2000, which is a National Stage Application filed under 35 U.S.C. §371 of PCT/US98/21061 filed on Oct. 7, 1998, which claims priority form Provisional Application 60/061,613 filed Oct. 10, 1997.

SCOPE OF THE INVENTION

This invention covers intermediates and a synthetic route for making 4-cyano-4-(3-cyclopentyloxy-4-methoxyphenyl) cyclohexanoic acid and its analogs. This acid and its named analogs are selective for inhibiting the catalytic site in the phosphodiesterase isoenzyme denominated IV (PDE IV hereafter) and as such the acids are useful in treating a number of diseases which can be moderated by affecting the PDE IV enzyme and its subtypes.

AREA OF THE INVENTION

Bronchial asthma is a complex, multifactorial disease characterized by reversible narrowing of the airway and hyper-reactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all major components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The process and intermediates of this invention provide a means for making certain 4-substituted-4-(3,4-disubstitutedphenyl)cyclohexanoic acids which are useful for treating asthma, and other diseases which can be moderated by affecting the PDE IV enzyme and its subtypes. The final products of particular interest are fully described in U.S. Pat. No. 5,552,483 issues Sep. 3, 1996. The information and representations disclosed therein, in so far as that information and those representations are necessary to the understanding of this invention and its practice, in total, are incorporated herein by reference.

SUMMARY OF THE INVENTION

This invention relates a method for making a compound of formula I

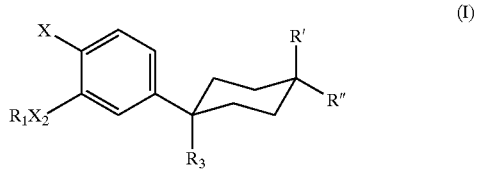

where $R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $YR_2$, halogen, nitro, $NH_2$, or formyl amine;

$X_2$ is O or $NR_8$;

Y is O or $S(O)_{m'}$;

m' is 0, 1, or 2;

$R_2$ is independently selected from —$CH_3$ or —$CH_2CH_3$ optionally substituted by 1 or more halogens;

$R_3$ is hydrogen, halogen, $C_{1-4}$ alkyl, $CH_2NHC(O)C(O)NH_2$, halo-substituted $C_{1-4}$ alkyl, —$CH=CR_8R_{8'}$, cyclopropyl optionally substituted by $R_{8'}$, CN, $OR_8$, $CH_2OR_8$, $NR_8R_{10}$, $CH_2NR_8R_{10}$, C(Z')H, $C(O)OR_8$, $C(O)NR_8R_{10}$, or $C\equiv CR_8$;

$R_8$ is hydrogen or $C_{1-4}$ alkyl optionally substituted by one to three fluorines;

$R_{8'}$ is $R_8$ or fluorine;

$R_{10}$ is $OR_8$ or $R_{11}$;

$R_{11}$ is hydrogen, or $C_{1-4}$ alkyl optionally substituted by one to three fluorines;

Z' is O, $NR_9$, $NOR_8$, NCN, $C(—CN)_2$, $CR_8CN$, $CR_8NO_2$, $CR_8C(O)OR_8$, $CR_8C(O)NR_8R_8$, $C(—CN)NO_2$, $C(—CN)C(O)OR_9$, or $C(—CN)C(O)NR_8R_8$;

R' and R" are independently hydrogen or —C(O)OX where X is hydrogen or metal or ammonium cation;

which method comprises:

a) combining a Group I(a) or Group II(a) metal halide, with an aprotic dipolar amide-based solvent and water and a compound of formula A or B,

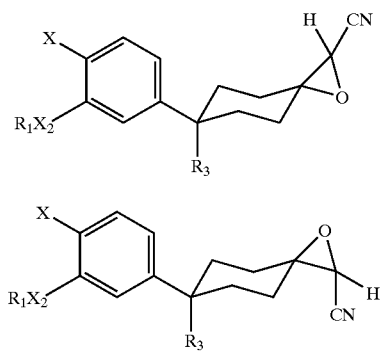

where $R_1$, $R_3$, $X_2$ and X are the same as for formula (I);

b) heating the combination to a temperature of at least about 60° for several hours, optionally under an inert atmosphere;

c) precipitating out a compound of formula (I) by adding a strong base to said combination;

d) removing the amide-based solvent and water from said precipitate, and optionally
1) purifying further the precipitate, or
2) acidifying the precipitate to obtain the free acid.

SPECIFIC EMBODIMENTS OF THE INVENTION

This process involves the synthesis of certain 4-substituted-4-(3,4-disubstitutedphenyl)cyclohexanoic acids. It allows for converting a cyanoepoxide to its corresponding homologated acid via the use of a Group I(a) or II(b) salt intermediate.

The compounds which are made by this process are PDE IV inhibitors. They are useful for treating a number of diseases as described in U.S. Pat. No. 5,552,438 issued Sept. 3, 1996.

The preferred compounds which can be made by this process are as follows:

Preferred $R_1$ substitutents for the compounds of all named formulas are $CH_2$—cyclopropyl, $CH_2$—$C_{5-6}$ cycloalkyl, $C_{4-6}$ cycloalkyl unsubstituted or substituted with $OHC_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

Preferred X groups for Formula (I) or (II) are those wherein X is $YR_2$ and Y is oxygen. The preferred $X_2$ group for Formula (I) is that wherein $X_2$ is oxygen. Preferred $R_2$ groups are a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Most preferred are those compounds wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl; and $R_3$ is CN.

The lithium salt of these compound represent a sub-set of preferred compounds. In particular the lithium salt of 4-cyano-4-(3-cyclopentyloxy-4-methoxyphenyl)-r-1-cyclohexanecarboxylic acid, i.e., lithium-4-cyano-4-(3-cyclopentyloxy-4-methoxyphenyl)-r-1-cyclohexanecarboxylate represents a preferred embodiment. More particularly, the compound cis-lithium4-cyano4-(3-cyclopentyloxy-4-methoxyphenyl)-r-1-cyclohexanecarboxylate is most preferred.

The carboxylate is made by opening the epoxide with a Group I(a) or II(a) metal halide to get the acyl nitrile which hydrolyzes to the acid in the presence of water. A problem in preparing the acid from the acyl nitrile is that when the carboxylate is formed from the acyl nitrile, hydrogen cyanide (HCN) is generated. The challenge is one of removing this HCN in a cost-effective way. A feature of this invention is a means for effecting a more efficient removal of HCN. It has been discovered that if the reaction is run in an aprotic dipolar amide-based solvent containing water, when a strong base is added a cyanide salt forms and remains in solution and the carboxylate salt which forms at the same time precipitates out of solution. This permits one to collect the precipitate and remove the solvent, and by that means remove most or essentially all of the cyanide salt from the alkanoic acid salt precipitate. This avoids having to run an extra purification step, such as oxidizing the HCN.

The Group I(a) or II(a) metal halides used in this invention are any of the halides of the alkali metals and the alkali earth metals, i.e., lithium, sodium, potassium, rubidium, cesium or francium; and beryllium, magnesium, calcium, strontium, barium, or radium. The preferred metals are lithium and magnesium. The halides include fluoride, chloride, bromide and iodide. The preferred halide is bromide. Lithium and magnesium halides are preferred. Lithium bromide and magnesium brornude are most preferred. Lithium bromide is particularly preferred.

In regards to the amide-based solvents, they are illustrated by the likes of dimethylformamide (DMF), dimethylacetamide, and N-methyl pyrrolidinone. DMF is most preferred. A second organic solvent can be used in addition to the amide-based solvent. For example acetonitrile has been used successfully in the reaction illustrated below. Normally water is added to the reaction pot as it hydrolyzes the acyl nitrile in situ to give the alkanoic acid. Hence a further preferred embodiment of this invention is to use an aprotic dipolar solvent which is water miscible. DMF, dimethylacetamide, and N-methyl pyrrolidinone meet this standard. While it is essential to have water in the reaction medium, the amount of water can vary widely. The reaction goes even when a minor amount of water is present. It is preferred to have at least 0.1% by weight/weight (wt/wt) present in the reaction vessel, calculated on the basis of both the liquids and the solids, if any, present in the vessel. A more preferred amount of water is at least about 1% wt/wt, and most preferably about 1–5% water by wt/wt. While not all possible combinations of water and amide-based solvent systems have been tested, it is known that the reaction will proceed with 20% water (wt/wt). Hence it is believed that even higher percentages of water can be used. Optimization of the organic solvent-to-water ratios can be achieved by the skilled practioner. The use of any amount of water in combination with an amide-based solvent is considered to be within the scope of this invention.

The reaction can be run at any temperature above about 60° C. Since there are numerous combinations of amide-based solvent and water that can be used, it is not practical to set an exact upper limit to the temperature since that will vary based on solvent selection and the ratio of the selected solvents.

The Group I(a) or II(a) metal halide opens the epoxide to give an acyl nitrile. It is hydrolyzed to the acid in the presence of water. But rather than isolate the free acid, an insoluble salt of the carboxylate is formed by adding about 2 or more equivalents of a strong base to the reaction vessel. This base forms two salts, a salt of the cyclohexanoic acid and a salt of HCN which is released in the hydrolysis of the acyl nitrile group. The metal cyanide it turns out is soluble in the solvent and the salt of the alkanoic acid precipitates out of solution. This makes it possible to separate the alkanoic acid salt from the cyanide salt by simply removing the solvent. The invention can be practiced using less than 2 equivalents of base, but that would possibly result in loss of the alkanoic acid because it would not precipitate out of solution, undesirable from an economic standpoint. And unreacted HCN could contaminate the alkanoic acid that did precipitate out of solution. Hence the preferred practice is to use 2 or more equivalents of the base.

A strong base for the purposes of this invention is any base that will form a salt with the cyanide ion. One can use any base strong enough to form these salts, formation of the cyanide salt is the more critical of the two criteria for determining if a particular base is useful in this step. Inorganic hydroxides are preferred. For example one can use LiOH, NaOH, or KOH. One can also use ammonium salts, for example tetra-alkylammonium hydroxides or $NH_4OH$. Lithium hydroxide is preferred because the lithium cyanide salt is highly soluble in the aqueous aprotic dipolar amide-based solvent, and thus effects more efficient and more complete removal of the cyanide ion from the acid salt when the armide-based solvent is removed. Lithium cyanide is more soluble in DMF than is sodium cyanide or potassium cyanide. So it is more advantageous to make lithium the cation in the strong base in the salt-forming step of the process.

A perferred practice of this invention is one in which the solvent(s) are charged to the reaction vessel, lithium bromide is added, and then the epoxide. Once the reaction has gone to completion essentially, two or more equivalents of an aqueous solution of lithium hydroxide are added, the cyclohexanoic acid salt is precipitated out of solution and filtered out, and the solvent discarded. The lithium salt of the cyclohexanoic acid can be further purified if needs be to remove residual contaminants such as cyanide salts, or converted to the acid by dissolving or suspending the salt in a solvent and acidifying that material to obtain the free acid.

A representative schematic of the process is set out in Scheme I and Scheme II. These graphical representations use specific examples to illustrate the general methodology used in this invention.

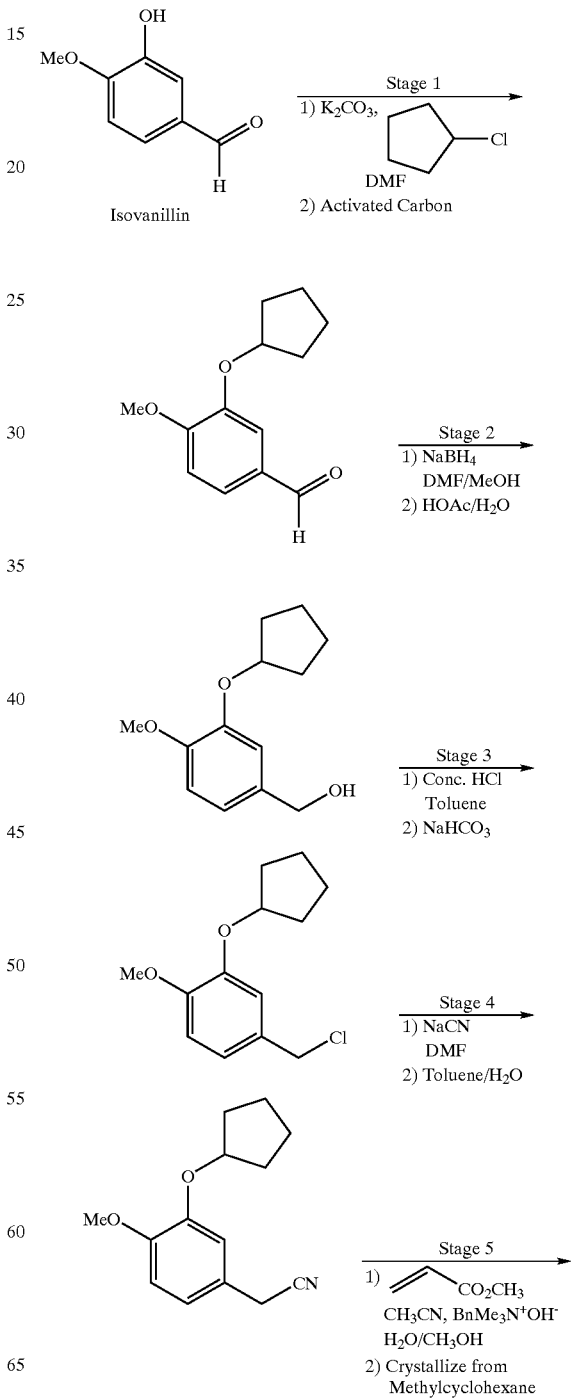

Scheme I

Scheme II illustrates a second very similar set of conditions that can be used in this invention. This scheme follows the same route as the one outlined in Scheme I; some of the conditions in certain steps are changed.

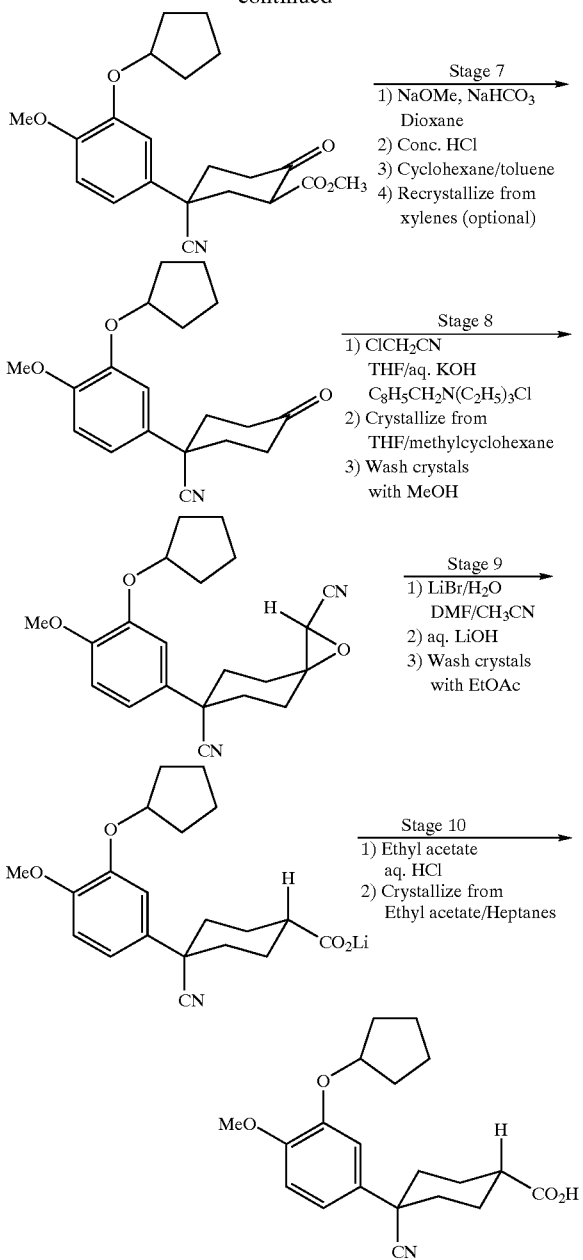

The chemistries illustrated in Scheme I are set out in a co-pending U.S. application which has been assigned U.S. Ser. No. 60/061613 (filed Feb. 12, 1997) and also filed as PCT application serial number PCT/US98/02749 designating inter alia the U.S.; it has been published as WO98/34584. That application is incorporated herein by reference, particularly as regards the chemistries underpinning steps 1–7.

The chemistries in Scheme II are set out in PCT application number PCT/EP98/05504 filed Aug. 26, 1998 which, inter alia, designates the U.S. as a selected State. The full disclosure of that application is incorporated herein by reference. In addition the details of this second set of chemistries are given below.

A general description of the chemistries in Schemes I and II follows:

A mixture of cyclopentyl chloride, isovanillin and potassium carbonate in dimethylformamide is stirred at about 125° C. until formation of the cyclopentyloxy product is deemed to be complete (approximately 2 hours). The mixture is cooled to 20–25° C., the solid (potassium chloride and potassium bicarbonate) is removed by centrifugation and is washed with methanol before being discarded. The dimethylformamide liquors and methanol wash are combined for use in the next step.

The solution of the cyclopentyloxy compound in dimethylformamide and methanol is cooled to about 0° C. and treated with sodium borohydride (approximately 1.5 hours). The temperature is maintained below 5° C. After that the mixture is stirred at 0 to 10° C. for 30 minutes and at 25–30° C. until the reduction reaction is deemed to be complete (approximately 1 hour). Acetic acid 50% is added to destroy the excess borohydride and the dimethylformamide and methanol are removed by distillation in vacuo. After cooling to 20–25° C. the mixture is partitioned between water and toluene. The toluene phase, containing the alcohol is washed with demineralised water, passed through a filter for use in the next step.

The solution of alcohol in toluene is treated with concentrated hydrochloric acid (min 36%) at 15 to 25° C. The organic phase, containing the chloro compound is separated and treated with sodium bicarbonate to neutralize the HCl traces. The solid (sodium chloride, sodium bicarbonate) is removed by filtration.

The solution of the chloro compound is concentrated by distillation in vacuo. After cooling to about 20° C., demineralised water, tetrabutylammonium bromide and sodium cyanide are added. After that the mixture is heated to 80° C. and stirred at this temperature until the cyanidation reaction is deemed to be complete (approximately 2 hours).

After cooling to <60° C. the mixture is partitioned between water and toluene. The toluene phase, containing the cyano compound is washed at 30 to 25° C. with demineralised water, distilled in vacuo to minimum volume and to this is added acetonitrile. The product solution in acetonitrile is used directly in the next step.

Solutions of methyl acrylate in acetonitrile and Triton B and acetonitrile are prepared. About 16.6% of the methyl acrylate solution is added to the cyano compound solution at <25° C. About 12.5% of the Triton B solution is the added, the mixture is stirred for some minutes and then cooled back to <25° C. This addition sequence is repeated three more times, then the final 33% of the methyl acrylate solution and the final 50% of the Triton B solution are added in two portions. The reaction mixture is stirred at 20 to 25° C. until the reaction is deemed to be complete (approximately 2–3 hours). The acetonitrile is removed by vacuum distillation to minimum volume. The mixture is partitioned between cyclohexane/toluene and water at 50° C. The cyclohexane/toluene phases, containing the pimelate is aged for about 1 hour at about 0° C.

The product is isolated by centrifugation and washed with cold (<0° C.) cyclohexane/toluene. The wet cake vacuum dried at max 50° C. to give the pimelate as an off white to beige powder.

A 29% methanolic solution of sodium methoxide is added in one lot to a solution of the pimelate in dioxane. The mixture is heated to about 75° C. (reflux) and maintained at this temperature until formation of the 2-carbomethoxycyclohexan-1-one is deemed complete (approximately 1 hour). Much of the methanol is distilled out and replaced with dioxane. Sodium bicarbonate and demineralised water are added to the. the mixture is heated to reflux (about 85 to 88° C.) and maintained at this temperature until formation of the cyclohexan-1-one is deemed to be complete (approximately 10 hours).

After that the mixture is cooled to <60° C. and concentrated hydrochloric acid solution is added to reduce the pH from >10 to 7.5

Much of the dioxane and methanol is removed by distillation in vacuo. After that the mixture is partitioned between cyclohexane/toluene and water at about 70° C. The organic phase, containing the ketone is washed twice with demineralised water at about 70° C.

The product solution is cooled to 10° C. and aged for about 1 hour at 9 to 11° C. The product is isolated by filtration and washed with cold (10° C.) cyclohexane/toluene. the wet cake is vacuum dried at max 50° C. to give the ketone as an off white powder.

The dicarbonitrile is prepared from the ketone by treating the ketone with chloroacetonitrile in the presence of an inorganic base and a catalytic amount of benzyltriethylammonium chloride (BTEAC). The ketone and a slight excess of chloroacetonitrile in a suitable solvent such as THF is charged into a mixture of strong base (aqueous potassium hydroxide) and BTEAC and a water miscible solvent such as tetrahydrofuran at reduced temperature, about 0° C. or thereabouts. The reaction is maintained at about that temperature for the duration of the reaction, usually about 1 hour. The product can be isolated or used as a crude oil.

The dicarbonitrile is converted to the cyclohexanecarboxylic acid using a Group I(a) or II(a) metal halide. This reaction is carried out by charging a vessel with solvents; in this instance exemplified by DMF, acetonitrile and water, and the Group I(a) or II(a) metal halide (preferably about 1.5 equivalents), LiBr is illustrated; sweeping the vessel with an inert gas; adding the dicarbonitrile A or B, or a mixture of A and B; and heating the vessel and its contents to about 100° C. for a number of hours, 8 hours being an example. The reaction is diluted with DMF and optionally water. LiOH dissolved in water is added (about a 50% molar excess is preferred). A suspension is formed. This is stirred at a slightly elevated temperature(40 to 80° C.) for about an hour or so. The lithium salt is recovered by conventional means.

The acid is prepared, for example, by suspending the lithium salt in an organic solvent of the likes of ethyl acetate, and treating the suspension with aqueous mineral acid. The organic solvent is then recovered, washed, and concentrated. The product is isolated by conventional means.

The following examples are provided to illustrate specific embodiments of the invention, not to limit it. What is reserved to the inventors is set forth in the claims appended hereto.

SPECIFIC EXAMPLES

Example 1

Preparation of 3-Cyclopentyloxy-4-methoxybenzaldehyde

A mixture of cyclopentyl chloride (8.48 g, 0.08 moles), isovanillin (6.12 g, 0.04 moles) and potassium carbonate (1.1 g, 0.08 moles) in dimethylformamide (4.04 g) was stirred in the reactor (100 mL) at 120 to 125° C. for 1.5 hours. A sample was taken to verify the batch conversion. Result (GC): 0.5 area % isovanillin (target:≦1.0 area %). The mixture was cooled to 20° C. and filtered to remove the solid (potassium bicarbonate, potassium chloride). The wet cake was washed with methanol.

Example 2

Preparation of 3-Cyclopentyloxy-4-methoxybenzyl Alcohol

The dimethylformamide liquors and methanol wash from Example 1 were combined and retransferred into the cleaned reactor. An additional amount of methanol (8.52 g) was added and the batch was cooled to 0° C. Sodium borohydride (0.49 g, 0.0129 moles) was added in small portions over 1 hour and 10 minutes maintaining the temperature between 4 and 9° C. The batch was stirred at 7.2 to 10° C. for 30 minutes and then heated to 25° C. A sample was taken after 110 minutes stirring at 25 to 31° C. and analysed (GC) and the reaction was deemed to be complete. Acetic acid 50% (1.80 g) was charged to the reactor to quench any remaining sodium borohydride. The batch temperature of 24 to 25° C. was maintained during this charge. The dimethylformamide and methanol were removed by distillation in vacuo (end of distillation: 58° C., 6 mbar). After cooling to 20–25° C. the mixture was partitioned between water (3.13 g) and toluene (28.07 g). The toluene phase (containing the captioned compound) was washed with demineralised water (2.65 g).

Example 3

Preparation of 4-Chloromethyl-2-cyclopentyloxy-1-methoxybenzene

The toluene solution from Example 2 was cooled to 20° C. and concentrated hydrochloric acid (37.5%; 9.80 g) was added keeping the temperature between 20 and 22.7° C. A sample was taken 40 minutes after the addition was complete and analysed (GC) and the reaction was deemed to be complete. The phases were allowed to separate and the lower, aqueous phase discarded. Sodium bicarbonate (1.20 g) was charged to the reactor to neutralize the remaining hydrochloric acid. After stirring for 15 minutes the mixture was cooled to 23° C. and filtered to remove the solid (sodium bicarbonate, sodium chloride). A part of the toluene (17.07 g) was removed by distillation in vacuo (end of distillation: 28° C., 7 mbar).

Example 4

Preparation of 4-Cyanomethyl-2-cyclopentyloxy-1-methoxybenzene

After cooling the solution from Example 3 to <25° C. tetra-butylammonium bromide (0.205 g, 0.63 mmoles), demineralised water (2.775 g) and sodium cyanide (1.976 g, 0.039 moles) were added, the mixture was heated to 80° C. and then stirred at 78.1 to 80.4° C. for 1 hour and 50 minutes. A sample was taken to verify the batch conversion.

Toluene (5.841 g) and demineralised water (8.76 g) were added, the phases were allowed to separate (at about 54° C.) and the lower, aqueous phase discarded. The toluene phase (containing the product) was washed with demineralised water (13.32 g). The toluene was removed by distillation in vacuo (end of distillation: 55° C., 1 mbar).

Example 5

Preparation of Dimethyl-4-cyano4-(3-cyclopentyloxy-4-methoxy-phenyl)pimelate The cyanomethyl compound prepared in Example 4 (9.05 g at 85.4%; 7.73 g at 100%; 0.0334 moles) was charged in the reactor (0.5 L) at room temperature. Acetonitrile (28.56 g) and demineralised water (0.07 g) was charged to the reactor. Solutions of methyl acrylate (6.88 g, 0.029 moles) in acetonitrile (4.02 g) and methanolic Triton B (40.2% 0.94 g, 2.269 mmoles Triton B) in acetonitrile (4.06 g) were prepared. A first portion, about 16.6% of the methyl acrylate solution (1.81 g) was added at 20° C. A first portion, about 12.5% of the Triton B solution (0.63 kg) was then added. The batch temperature after the addition was 31° C. A second portion, about 16.6% of the methyl acrylate solution (1.82 g) was added at 28° C. A second portion, about 12.5% of the Triton B solution (0.63 g) was then added. The batch temperature after the addition was 36° C. A third portion, about 16.6% of the methyl acrylate solution (1.81 g) was added at 35° C. A third portion, about 12.5% of the Triton B solution (0.62 g) was then added. The batch temperature after the addition was 32° C. A fourth portion, about 16.6% of the methyl acrylate solution (1.81 g) was added at 32° C. A fourth portion, about 12.5% of the Triton B solution (0.63 g) was then added. The batch temperature after the addition was 36° C. A fifth portion, about 33.2% of the methyl acrylate solution (3.64 g) was added at 34° C. A fifth portion, about 25% of the Triton B solution (1.25 g) was then added. The batch temperature after the addition was 38° C. The last portion, about 25% of the Triton B solution (1.25 g) was then added. The batch temperature after the addition was 36° C. The reaction mixture was stirred for 1.5 hours at 20–25° C. The acetonitrile was removed by distillation in vacuo (end of distillation: 59° C., 20 mbar). The mixture was partitioned at about 50° C. between cyclohexane/toluene (1145.9/254.6 g) and water (559.8 g). The cyclohexane/toluene phase (containing the product was washed with demineralised water (559.8 g) at 50 to 52° C. To crystallize the captioned product, the batch was cooled over 50 minutes to 0° C. The batch was then seeded with pimelate and aged for 1 hour at −1 to 1° C. The pimelate was filtered and washed with cyclohexaneltoluene (6.51 g/1.44 g) and recovered by conventional means.

Example 6

Preparation of 4-Cyano-4-(3-cyclopentyloxy-4-methoxyphenyl)cyclohexan-1-one

The pimelate made in Example 5 (76.52g, 1,8112 moles) was charged into the reactor (100 mL). Dioxane (2214 g) and a 29.1% methanolic of sodium methoxide (0.44 g, 24 mmoles) were added. The mixture was heated to reflux (77° C.) and stirred at this temperature for 1 hour. A sample was taken to verify the batch conversion. The methanol was removed by distillation (16.82 g distillate) to a bottom temperature of 97° C. the loss of dioxane during this distillation was compensated by adding of fresh dioxane (121.6 g). Sodium bicarbonate (22.2 g, 26. mmoles) and demineralised water (2.47 g) were added. The mixture was heated to reflux (87° C.) and stirred at about to 87° C. for 10 hours. A sample was taken to verify the batch conversion. The content of the reactor was cooled to 78° C. Dioxane (0.13 g) and demineralised water (0.12 g) were added to simulate a flush. After cooling to <60° C. concentrated hydrochloric acid (37%, 0.265 g) was added to adjust the pH to 7.5. The dioxane, methanol and apart of water (27.73 g distilled) were removed by vacuum distillation (end of distillation: 66° C., 305 mbar).

Under stirring, cyclohexane (180.0 g) and toluene (65.5 g) were charged to the reactor. The mixture was heated to 70° C. and the phases were allowed to separate at 70° C. and the lower, aqueous phase was discarded. The organic phase, containing the captioned ketone was washed in two portions with demineralised water (1 69.4 g total) at about 70° C. Cyclohexane (165.0 g) was added to the reactor to simulate a flush. To crystallize the product, the batch was cooled to 10° C. over 1 hour. Then it was aged for 6 hours at 9 to 11° C. to complete the crystallization. The product batch was filtered and washed with cyclohexane/toluene (81.5 g/27.2 g).

Example 7

Preparation of cis-6-[3-(Cyclopentyloxy)-4-methoxyphenyl)]-1-oxaspiror[2.5]octane-2.6-dicarbonitrile A 500 mL round bottom flask equipped with an overhead stirrer, internal thermometer, and a nitrogen inlet was flushed with nitrogen. The flask was charged with 50% potassium hydroxide in water (22.0 g) and tetrahydrofuran (55.0 mL). While stirring at room temperature, benzyltriethylammonium chloride (0.81 g, 35 mmol, 0.05 equivalent) was added. The solution was cooled to 0° C. To a pressure-equalizing addition funnel was charged a solution containing tetrahydrofuran (55.0 mL), 4-cyano-4-(3-cyclopentyloxy-4-methoxyphenyl) cyclohexan-1-one (23.0 g, 73 mmol, 1.0 equivalent), and chloroacetonitrile (5.9 g, 78 mmol, 1.07 equivalent) at room temperature. While stirring the flasks contents at 0° C., the solution in the pressure addition funnel was added over 15 minutes. The temperature was maintained between and 5° C., and stirred for one hour. The reaction was warmed to 25° C., diluted with water (90.0 mL), and ethyl acetate (90.0 mL). The solution was stirred and allowed to settle for 30 minutes. The layers were separated, the organic layer was isolated, and concentrated by vacuum distillation to a residue. Methylcyclohexane/ THF (5:1) (54.0 mL) was added and the solution was heated to 60° C. then cooled to 20° C. over 90 minutes; the product began to crystallize at about 40° C. The suspension was then cooled to 0° C. and held at −0 to 5° C. for two hours. The product was filtered and washed with a methanol mixture (46.0 mL) at 0° C. The product was dried to afford the captioned product as a white crystalline solid.

Example 8

Preparation of cis-Lithium-4-cyano-4-(3-cyclopentyloxy-4-methoxyphenyl)-r-1-cyclohexanecarboxylate, 2

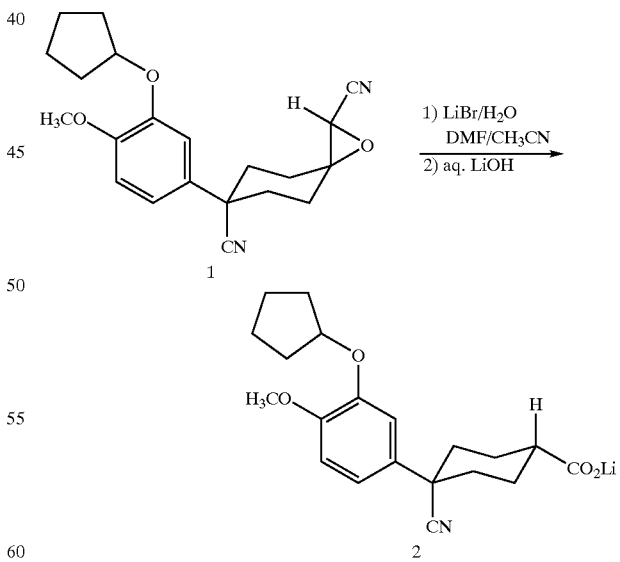

To a 1.0 L, 3-neck round bottom flask equipped with an overhead stirrer, internal thermometer and a reflux condenser connect to a caustic scrubber was charged dimethylformamide (200 mL), acetonitrile (200 mL), lithium bromide (32.4 g, 0.37 mol) and water (5.6 g, 0.31 mol). The suspension was stirred until a solution was evident, followed by the addition of cis-6-[3—(cyclopentyloxy)-4-methoxyphenyl)]-1-oxaspiro[2.5]octane-2,6-dicarbonitrile, 1, (90.0 g, 0.25 mol). The contents of the flask were heated between 90 and 95° C. for 8 to 12 hours. The reaction was cooled to 60° C. and diluted with dimethylformamide (270 mL). To the amber solution (60° C.) was quickly added an aqueous solution of lithium hydroxide (21.65 g, 0.51 mol of lithium hydroxide monohydrate dissolved in 112.5 mL of water). The suspension was stirred at 60° C. for 1 hour, cooled to 5° C., and held at 5° C. for 1 hour. The suspension was filtered, washed with ethyl acetate (100 mL) and air dried to provide 2 in 79.5% corr yield.

Example 9

Preparation of cis-4-cyano-4-(3-cyclopentyloxy-4-methoxyphenyl)-r-1-cyclohexanecarboxylate, 3

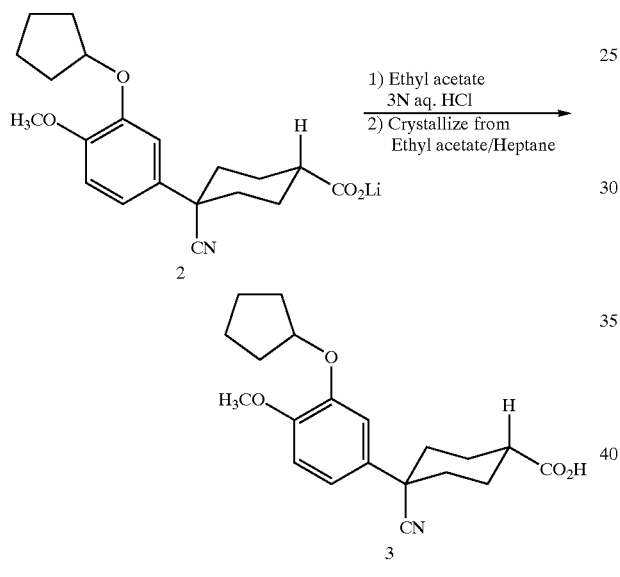

To a 1.0 L, 3-neck round bottom flask equipped with an overhead stirrer and an internal thermometer was added cis-lithium-4-cyano-4-(3-cyclopentyloxy-4-methoxyphenyl)-r-1-cyclohexanecarboxylate, 2 (58.5 g, 0.167 mol) and ethyl acetate (500 mL). The light suspension was stirred at ambient temperature followed by the addition of 3N aqueous HCl (70 mL, 0.21 mol). The reaction was stirred for ten minutes and transferred to a separatory funnel. The organic layer was isolated and washed once with water (100 mL). The organic layer was isolated and filtered into a clean 1.0 L, 3-neck round bottom flask equipped with a distillation head and an overhead stirrer. The reaction was concentrated by distilling off ethyl acetate (200 mL). The contents of the flask were cooled to 60° C. followed by the addition of heptane (275 mL). The suspension was cooled to 5° C., held at 5° C. for 2 hours, filtered, and washed with cold (5° C.) heptane (50 mL). The product was dried in a vacuum oven to constant weight to afford 50.0 g (85%) of 3.

What is claimed is:

1. An improved process for preparing a compound of formula (I)

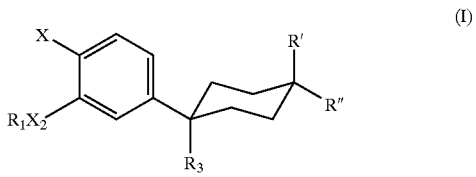

$R_1$ is —$(CR_4R_5)_rR_6$ wherein the alkyl moieties may be optionally substituted with one or more halogens;

r is 0 to 6;

$R_4$ and $R_5$ are independently selected from hydrogen or a $C_{1-2}$ alkyl;

$R_6$ is $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

X is $YR_2$, halogen, nitro, $NH_2$, or formyl amine;

$X_2$ is O or $NR_8$;

Y is O or $S(O)_{m'}$;

m' is 0, 1, or 2;

$R_2$ is independently selected from —$CH_3$ or —$CH_2CH_3$ optionally substituted by 1 or more halogens;

$R_3$ is hydrogen, halogen, $C_{1-4}$ alkyl, $CH_2NHC(O)C(O)NH_2$, halo-substituted $C_{1-4}$ alkyl, —CH=$CR_{8'}R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or C≡$CR_{8'}$ $R_8$ is hydrogen or $C_{1-4}$ alkyl optionally substituted by one to three fluorines;

$R_{8'}$ is $R_8$ or fluorine;

$R_{10}$ is $OR_8$ or $R_{11}$;

$R_{11}$ is hydrogen, or $C_{1-4}$ alkyl optionally substituted by one to three fluorines;

Z' is O, $NR_9$, $NOR_8$, NCN, C(—CN)$_2$, $CR_8CN$, $CR_8NO_2$, $CR_8C(O)OR_8$, $CR_8C(O)NR_8R_8$, C(—CN)NO$_2$, C(—CN)C(O)OR$_9$, or C(—CN)C(O)NR$_8R_8$;

R' and R" are independently hydrogen or —C(O)OX where X is hydrogen or Li;

which method comprises:
 a) combining a Group I(a) or Group II(a) metal halide, with an aprotic dipolar amide-based solvent and water and a compound of formula II(a) or II(b),

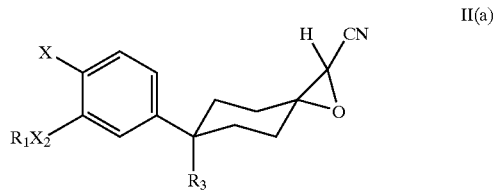

-continued

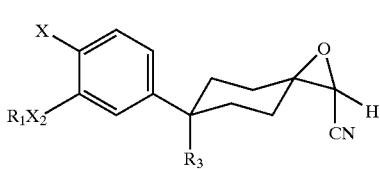

II(b)

where $R_1$, $R_3$, $X_2$ and X are the same as for formula (I)

b) heating the combination to a temperature of at least about 60° for several hours, optionally under an inert atmosphere;

wherein the improvement comprises:

c) precipitating out a compound of formula (I) by adding sufficient LiOH to said combination to form a compound of formula (I) where the X in —C(O)OX is Li;

d) removing the amide-based solvent and water from said precipitate, and optionally:
  i) purifying further the Li salt; or
  ii) acidifying the Li salt to obtain the free acid.

2. The process of claim 1 wherein in formula (I) $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl; and $R_3$ is CN.

3. The process of claim 1 wherein the Group I(a) or II(a) metal halide is lithium or magnesium halide.

4. The process of claim 1 wherein the Group I(a) or II(a) metal halide is lithium bromide or magnesium bromide.

5. The process of claim 1 in which the aprotic dipolar amide-based solvent is dimethylformamide, dimethylacetamide, or N-methyl pyrrolidinone.

6. The process of claim 1 wherein the Group I(a) or II(a) metal halide is lithium bromide and the amide-based solvent is dimethylformamide.

7. The process of claim 1 wherein water is present in an amount greater than 0.1% by weight/weight of the contents of the reaction vessel.

8. The process of claim 1 wherein the compound of formula II(a) or II(b) is cis-6-[3-(cyclopentyloxy)-4-methoxyphenyl)]-1-oxaspiro[2.5]octane-2,6-dicarbonitrile.

* * * * *